United States Patent
van Brug et al.

(10) Patent No.: US 10,578,545 B2
(45) Date of Patent: Mar. 3, 2020

(54) SPATIALLY RESOLVED AEROSOL DETECTION

(71) Applicant: Nederlandse Organisatie voor toegepast-natuurwetenschappelijk onderzoek TNO, 's-Gravenhage (NL)

(72) Inventors: Hedser van Brug, 's-Gravenhage (NL); Huibert Visser, 's-Gravenhage (NL)

(73) Assignee: Nederlandse Organisatie voor toegepast-natuurwetenschappelijk onderzoek TNO, 's-Gravenhage (NL)

(*) Notice: Subject to any disclaimer, the term of this patent is extended or adjusted under 35 U.S.C. 154(b) by 0 days.

(21) Appl. No.: 15/562,791

(22) PCT Filed: Mar. 30, 2016

(86) PCT No.: PCT/NL2016/050217
§ 371 (c)(1),
(2) Date: Sep. 28, 2017

(87) PCT Pub. No.: WO2016/159766
PCT Pub. Date: Oct. 6, 2016

(65) Prior Publication Data
US 2018/0284013 A1    Oct. 4, 2018

(30) Foreign Application Priority Data
Mar. 31, 2015   (EP) .................................. 15162031

(51) Int. Cl.
*G01N 21/21*   (2006.01)
*G01N 21/53*   (2006.01)
(Continued)

(52) U.S. Cl.
CPC ............ *G01N 21/21* (2013.01); *G01J 3/0208* (2013.01); *G01J 3/0224* (2013.01); *G01J 3/447* (2013.01);
(Continued)

(58) Field of Classification Search
CPC ................. G01N 21/21; G01N 21/538; G01N 2021/4711; G01N 2021/4704;
(Continued)

(56) References Cited

U.S. PATENT DOCUMENTS 3,399,591 A * 9/1968 Drougard ............. G02B 5/3083
356/366
4,198,123 A * 4/1980 Kremen ............... G02B 5/3083
356/317
(Continued)

OTHER PUBLICATIONS https://glory.giss.nasa.gov/aps/.*
(Continued)

*Primary Examiner* — Mohamed K Amara
(74) *Attorney, Agent, or Firm* — Leydig, Voit & Mayer, Ltd.

(57) ABSTRACT

An aerosol detector system is described for spatially resolved detection of an aerosol distribution in an area. The system includes a wide field polarization preserving telescope having telecentric imaging optics for imaging the earth surface onto a detector that receives phase stepped images from the telescope, A controller is arranged to provide a resulting image as a function of corresponding pixel values of the multiple images to produce an image at a spatially resolved polarization state corresponding to said aerosol substance.

5 Claims, 8 Drawing Sheets

(51) Int. Cl.
*G01J 3/02* (2006.01)
*G01J 3/447* (2006.01)
*G01N 21/17* (2006.01)
*G01N 21/47* (2006.01)

(52) U.S. Cl.
CPC ... *G01N 21/538* (2013.01); *G01N 2021/1793* (2013.01); *G01N 2021/4711* (2013.01)

(58) Field of Classification Search
CPC ... G01N 2021/1793; G01N 2021/4792; G01N 33/0027; G01N 21/31; G01N 21/314; G01N 21/39; G01J 3/447; G01J 3/0224; G01J 3/0208; G01J 4/04; G01J 3/36; G01J 3/42; G01J 3/4531; G01J 3/45; G01J 3/4532; G01J 3/28; G02B 5/3083; G02B 27/286; G02B 27/0018; G02B 5/30; G02B 23/00; G02B 2207/123
See application file for complete search history.

(56) References Cited

U.S. PATENT DOCUMENTS

| | | | | |
|---|---|---|---|---|
| 4,353,650 | A * | 10/1982 | Sommargren | G01B 11/303 356/369 |
| 4,586,782 | A * | 5/1986 | Sakuma | B41J 2/471 359/212.1 |
| 4,666,259 | A * | 5/1987 | Iizuka | G02B 17/0808 359/731 |
| 4,730,910 | A * | 3/1988 | Humphrey | A61B 3/156 359/601 |
| 5,249,080 | A * | 9/1993 | Watson | G02B 27/58 359/399 |
| 5,694,216 | A * | 12/1997 | Riza | G01B 9/02004 356/485 |
| 6,219,185 | B1 * | 4/2001 | Hyde | B64G 1/105 244/3.16 |
| 6,304,330 | B1 * | 10/2001 | Millerd | G01B 11/2441 356/495 |
| 6,498,869 | B1 * | 12/2002 | Yao | G02B 6/2706 359/494.01 |
| 7,042,610 | B1 * | 5/2006 | Berman | G02B 5/00 359/226.1 |
| 7,057,737 | B2 * | 6/2006 | Millerd | G01J 9/02 356/495 |
| 7,315,381 | B2 * | 1/2008 | Sesko | G01B 9/02081 356/493 |
| 7,402,785 | B2 * | 7/2008 | Barchers | G01J 9/00 250/201.9 |
| 7,675,684 | B1 * | 3/2010 | Weissman | G02B 27/0172 359/630 |
| 7,715,099 | B2 * | 5/2010 | Shih | G01J 1/04 216/24 |
| 7,864,333 | B1 * | 1/2011 | Olczak | G02B 27/286 356/491 |
| 7,929,215 | B1 * | 4/2011 | Grund | G02B 17/008 359/629 |
| 9,140,990 | B2 * | 9/2015 | Tanitsu | G02B 27/286 |
| 9,460,922 | B1 * | 10/2016 | Ahn | B23K 26/0604 |
| 2002/0018435 | A1 * | 2/2002 | Kim | G02B 5/3083 369/112.15 |
| 2002/0027719 | A1 * | 3/2002 | Kreuzer | G02B 5/3083 359/631 |
| 2002/0171829 | A1 * | 11/2002 | Yamashita | G01J 4/04 356/369 |
| 2003/0007149 | A1 * | 1/2003 | Yamamoto | G01J 3/02 356/328 |
| 2004/0213514 | A1 * | 10/2004 | Tanaka | G02B 27/0966 385/31 |
| 2005/0041288 | A1 * | 2/2005 | Liao | G02B 27/283 359/489.07 |
| 2005/0280806 | A1 * | 12/2005 | Oomori | G01N 21/21 356/237.2 |
| 2006/0066868 | A1 * | 3/2006 | Opsal | G01B 11/0641 356/495 |
| 2006/0146384 | A1 * | 7/2006 | Schultz | G02B 27/09 359/9 |
| 2006/0222041 | A1 * | 10/2006 | Moriwaka | B23K 26/0648 372/101 |
| 2006/0234848 | A1 * | 10/2006 | Kuehn | C03B 19/1453 501/54 |
| 2007/0014504 | A1 * | 1/2007 | Fiolka | G02B 27/286 385/11 |
| 2007/0159685 | A1 * | 7/2007 | Wagner | F41G 1/38 359/365 |
| 2010/0141959 | A1 * | 6/2010 | Kuchel | G01J 9/0215 356/521 |
| 2011/0300490 | A1 * | 12/2011 | Rachet | G02B 21/0032 430/322 |
| 2012/0170131 | A1 * | 7/2012 | Hengster | C03B 19/1469 359/642 |
| 2012/0257197 | A1 * | 10/2012 | Feldkhun | G01N 21/4795 356/301 |
| 2012/0262772 | A1 * | 10/2012 | Louradour | G02F 1/136277 359/238 |
| 2013/0100333 | A1 * | 4/2013 | Awatsuji | G03H 1/0443 348/335 |
| 2014/0267674 | A1 * | 9/2014 | Mertz | G01J 9/00 348/79 |
| 2015/0116812 | A1 * | 4/2015 | Matsumoto | G02B 21/0032 359/279 |
| 2017/0045397 | A1 * | 2/2017 | Schmidt | G01N 21/211 |
| 2018/0292310 | A1 * | 10/2018 | Kojima | G01N 21/21 |

OTHER PUBLICATIONS

Kokhanovsky et al., "Space-based remote sensing of atmospheric aerosols: The Multi-angle spectro-polarimetric frontier," Earth-Science Reviews, vol. 145, pp. 85-116, XP029169424 dated Feb. 28, 2015 (32 pages).

Manolis et al., "The MetOp Second Generation 3MI instrument," Proceedings of SPIE, vol. 8889, pp. 8889OJ-1 to 8889OJ-13, XP055210931 dated Oct. 16, 2013 (13 pages).

European Patent Office, International Search Report in International Application No. PCT/NL2016/050217 dated Aug. 23, 2016 (2 pages).

\* cited by examiner

SPATIALLY RESOLVED AEROSOL DETECTION

CROSS-REFERENCE TO RELATED APPLICATIONS

This patent application is a U.S. National Phase of PCT International Application No. PCT/NL2016/050217, filed Mar. 30, 2016, which claims priority to European Application No. 15162031.7, filed Mar. 31, 2015, the contents of which are expressly incorporated herein by reference in there entireties, including any references therein.

FIELD OF THE INVENTION

The invention relates to a method and system for spatially resolved aerosol detection, in particular in a satellite application that orbits the planet.

BACKGROUND OF THE INVENTION

Remote sensing, i.e. for instance to monitor particular aerosol concentrations in the Earth's atmosphere is carried out by an imaging satellite detector that captures multiple images of the Earth and calculate from these images a Degree of Linear Polarization (DoLP), the Angle of Linear Polarization (AoLP) and the radiometric intensity.

Satellites are orbiting the Earth at an altitude of typically between 400 and 800 km. These orbits are indicated as Low Earth Orbits (LEO). The speed of these satellites relative to the Earth is about 7 km/s. Since an integration time of about 1s is needed to arrive at a good enough Signal to Noise Ratio (SNR), an effective ground pixel on Earth will be about 5 km in flight direction. Most often some binning in the swath direction is used leading to square ground pixels of e.g. 5×5 km.

Scientists are asking for smaller ground pixels while keeping good SNR values. This is difficult since the scattering by the Earth is a constant, as is the output of the Sun, so the only way to decrease the ground pixel size is by moving towards larger entrance apertures and smaller f-numbers in the optical design. This leads to larger, heavier, and more expensive instruments.

An example of such an aerosol detection system by multi-polarisation imaging in a satellite application is found for instance in "The MetOP Second Generation 3MI instrument", Ilias Manolis, Proc. of SPIE Vol. 8889 88890J-1. Overlapping 2D images on the surface of Earth are recorded consecutively at regular points along an orbit and thus providing the means to sense the Top of Atmosphere radiance at different Observation Zenith Angles for each target. In this way ground pixels are measured at many angles and the angular distribution of the DoLP and intensity, and many characteristics of an aerosol distribution can be determined. In the disclosed device spectral channels within each module are recorded sequentially, while, for the polarized ones, three consecutive polarization measurements are taken with a linear polarizer oriented at +60, 0, and −60 degrees respectively for each channel.

The prior art device relies on a broadband telecentric design, wherein prior to detection a telecentric beam is projected through a spectral filter and polarization filters, the telecentric design ensuring a controlled optical functionality of the filters, in order to provide a reliable—per pixel detection of polarization.

A drawback of the prior art imaging device is that it relies on an extremely large aperture of the first lens in order to have a sufficient angle of view. This is necessary since in flight direction a number of subsequent measurements are carried out for different polarizations and colors, with the same equipment. This reduces the level of accuracy of the polarization detection, and renders the device very vulnerable for deterioration since the input is a wide angle lens of several centimeters. In relation therewith, the optical design is complex since it is designed for many wavelengths that are measured sequentially. This puts a high demand on the chromaticity of the system.

Instead of sequential imaging, another approach is to instantaneously measure a polarization state of the incoming light beam in a parallel measurement. For example, this beam may be distributed via a power splitter over multiple channels. In those channels, light can then be split into the s and p-polarized component. This will result in plural images of the earth, the one for s-, the other for p-polarized light. For example another output of the power splitter can be rotated 45 degrees in polarization and then also have to be dissolved in s- and p-components. From these four polarization stepped images, a degree of linear polarization can be determined, a direction of polarization, and the intensity.

With this approach the aim is to provide a better design of a spatially resolved polarization detector with lower input aperture in particular smaller than 4 mm which fulfills the criteria of compactness, where a desire exists to carry out the measurements in parallel for multiple wavelengths to obviate the problem of limited integration time for obtaining sufficient spatial resolution. Thus the problem is to provide an optical design that can be carried out in parallel, wherein the input aperture is limited to a value substantially smaller than 4 mm. This has an advantage that the optics can be optimized for a specific spectral range, so that polarization can be preserved and better accuracies can be obtained. It is also desired to provide a design that can easily be calibrated in space, which is non-trivial due to the working conditions.

SUMMARY OF THE INVENTION

The invention pertains to an aerosol detector system for spatially resolved detection of an aerosol distribution in an area, comprising: a wide field polarization preserving telescope having telecentric imaging optics for imaging the earth surface onto a detector; said detector receiving multiple polarization phase stepped images imaged by said telescope; and a controller coupled to the detector, arranged to provide a difference image as a function of corresponding pixel values of said multiple images to produce an image at a spatially resolved polarization state corresponding to said aerosol substance; wherein the telescope comprises a first telecentric imaging lens group and a wavelength filter positioned in a field image of the first telescope telecentric beam to define a spectral range of interest; the telescope further comprising: a converging lens group converging the beam to a pupil stop; relay optics including a second telecentric imaging lens group arranged to generate a telecentric beam; and splitter optics, comprising a power splitter, a polarization splitter and a retarder to create multiple polarization phase stepped images i.e. at different polarization angles, the detector comprising multiple image sensors positioned in imaging planes in said branches.

DETAILED DESCRIPTION OF EMBODIMENTS

Figure 1:
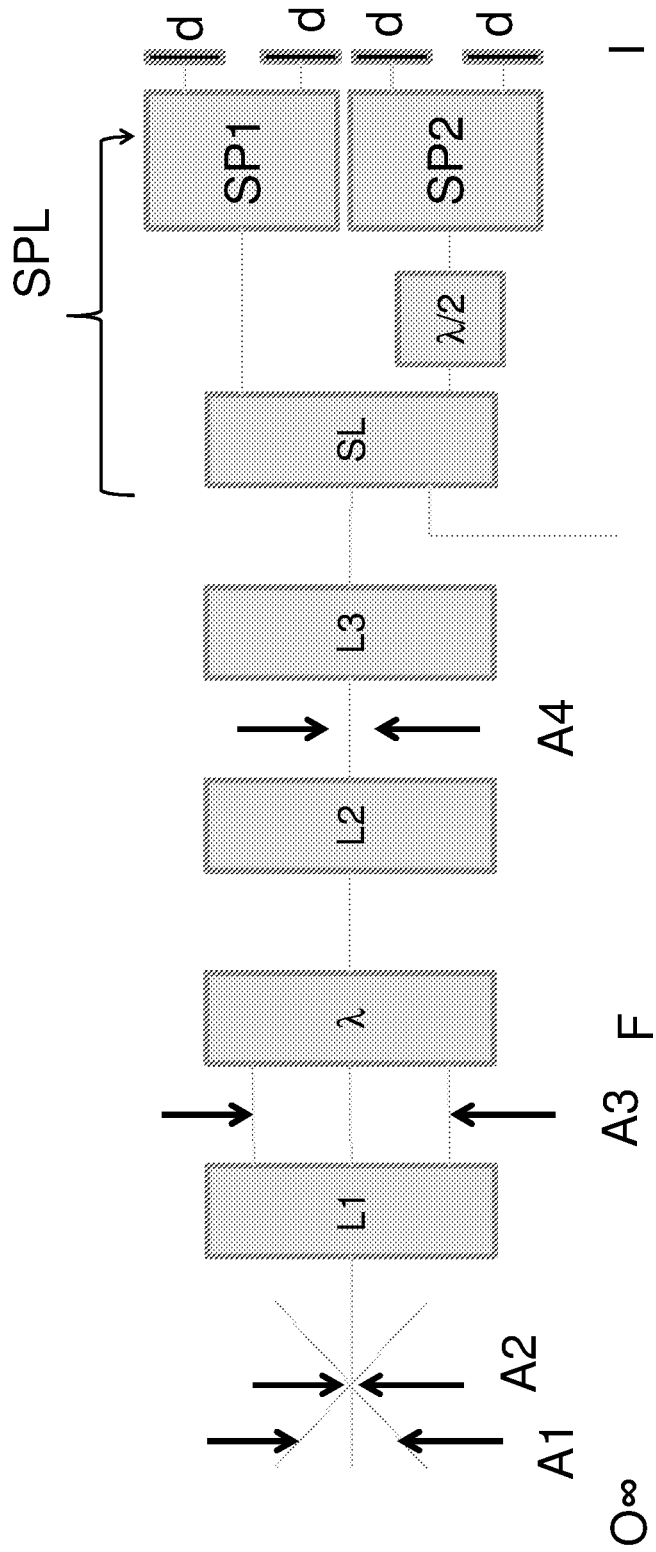
FIG. 1 describes in schematic detail a first embodiment.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

Throughout the application, any means for carrying out the disclosed methods, in particular, as further clarified below: means imaging, means for splitting, means for relaying can be implemented by optics that are known to the skilled person and may differ in form and structure to arrive at the same function; i.e. the function is physically implemented in optical elements such as mirrors, lenses and prisms. Furthermore, the identified controller functions may be implemented in hardware or software, to provide dedicated processing circuitry that processes input data read from system resources. A server function may e.g. be provided by a connected physical network device, but may also be formed as a virtual device, functioning in a network, and which may be implemented on a hardware resource that can be reached via network communication. These functions may be executed by one or more processors configured to perform operational acts in accordance with the present systems and methods, such as to provide control signals to the various other module components. The controller may comprise a processor that may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Any type of processor may be used such as dedicated or shared one. The processor may include microcontrollers, central processing units (CPUs), digital signal processor s (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the size and relative sizes of systems, components, layers, and regions may be exaggerated for clarity. Embodiments are described with reference to schematic illustrations of possibly idealized and/or intermediate structures of the invention.

Figure 2:
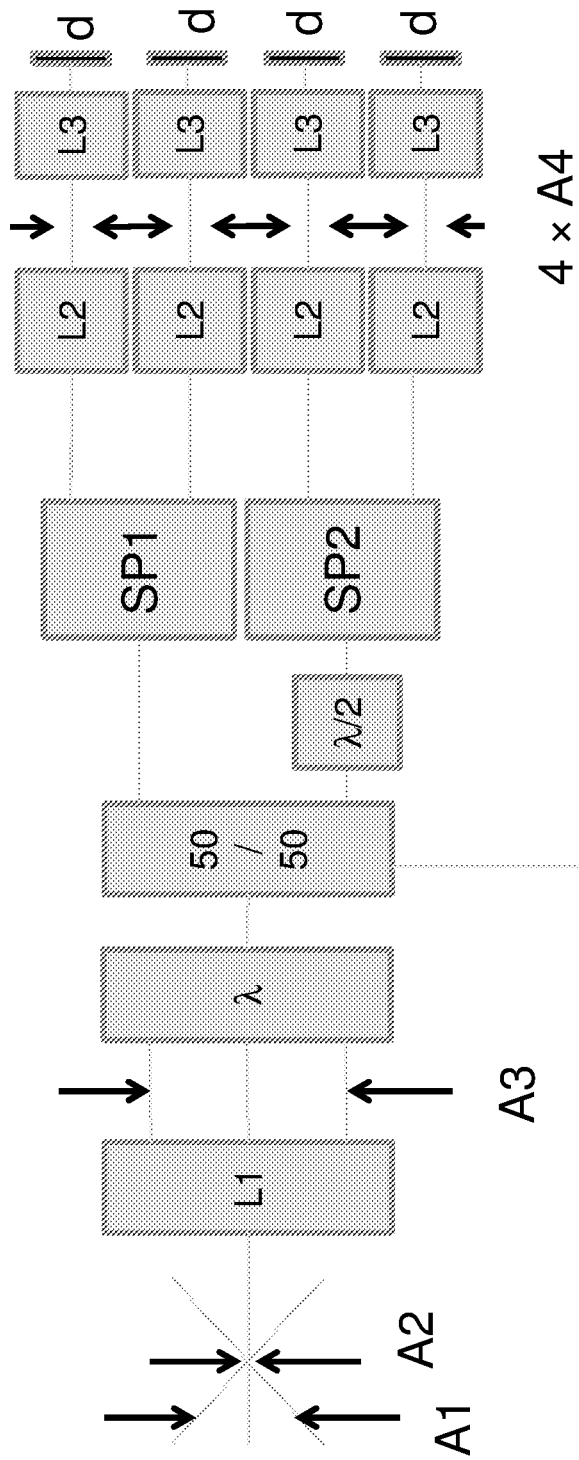
FIG. 2 shows a second embodiment in schematic detail.
Figure 3:
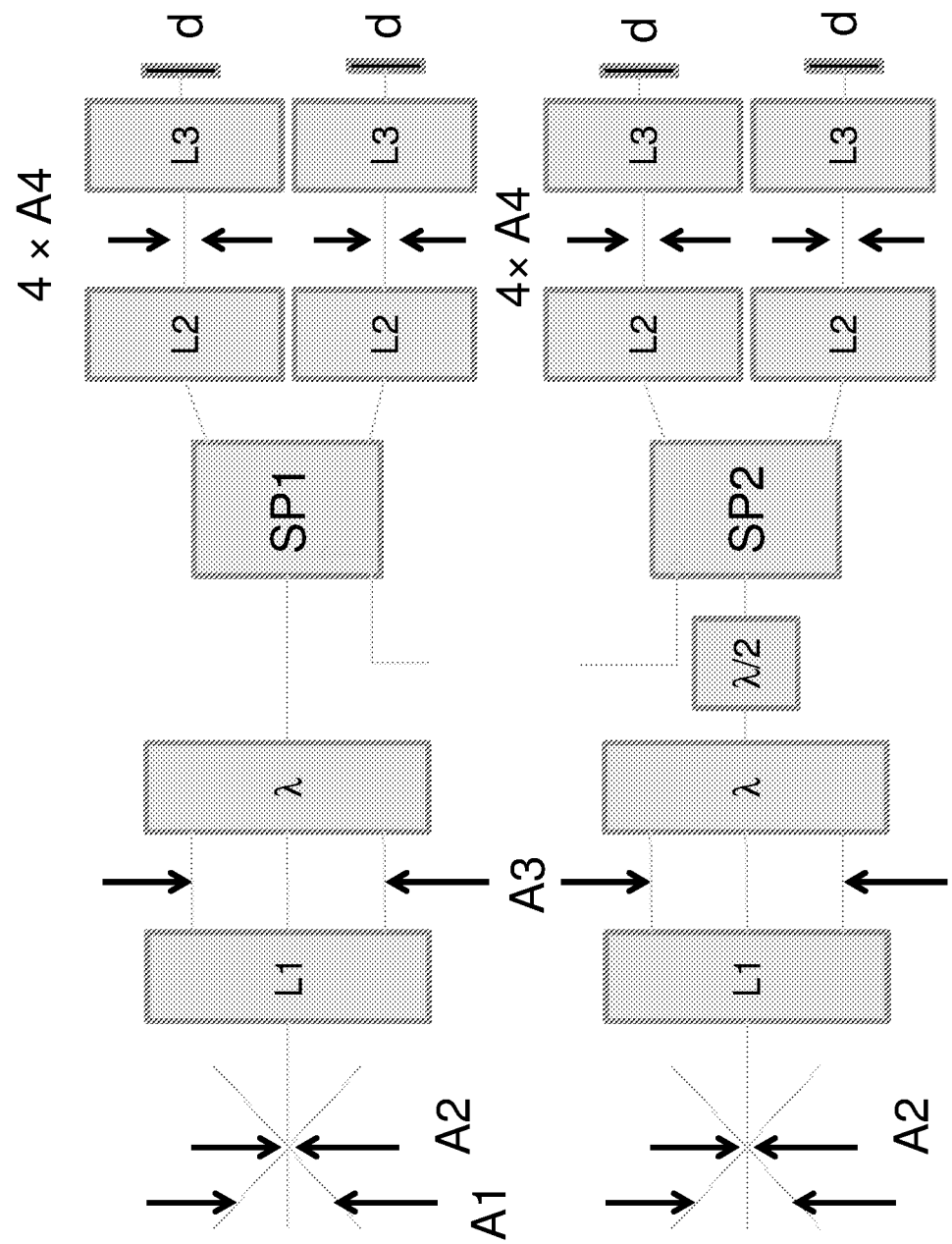
FIG. 3 shows another embodiment in some schematic detail.

In FIGS. 1-3 A1 denotes a slightly oversized input baffle; A2 an entrance pupil aperture; A3 a field stop and A4 a pupil stop.

FIG. 1 shows an aerosol detection scheme having an oversized entrance aperture of about 1 mm as a wide field polarization preserving telescope having telecentric imaging optics for imaging the earth surface onto detectors d placed at imaging plane I. A first telecentric imaging lensgroup L1 images the earth, object plane O at 'infinity' i.e. much larger than the imaging distance, on a wavelength filter, that can be provided as a movable filter elements or with a pattern of filter elements, to provide a wavelength filter A in a field image F close to field stop A3 of the first telescope telecentric beam to define a spectral range of interest. Due to the detector moving across the earth surface, a telecentric image can move through a patterned filter λ. Since the image of the Earth moves over the wavelength filter, a striped wavelength filter could be used to measure two wavelength band within a single module. The basic wavelength filter may be a band filter for a narrow wavelength band, leading to optimal polarization maintenance due to the fact that polarization neutral coatings are easier for smaller wavelength ranges. In the disclosed embodiment the field of view is about 112° and 64° in swath. In the first embodiment a converging lens group L2 is provided after the spectral filter A and converges the telecentric beam to the pupil stop A4, defining a real entrance pupil. Depending on the design, the pupil diameter A1 may be fairly small e.g. about 0,5-1,2 mm, providing a very small exposed area for the optical system which is favourable in terms of the optical system robustness. Next, a further telecentric imaging lens group L3 is provided, optionally provided with relay elements such as polarizing preserving folding mirrors, that images a telecentric image on the detector located at I.

The detector is comprised of four sensors d that are provided in the image plane I of the telescope. Splitter optics SPL are provided comprising polarization splitters SP1 SP2 for the selected wavelength range to split the telecentric beam into polarized beams; a further splitter SL; and a retarder λ/2 to create multiple phase stepped images at different polarizations. Prior to imaging, 50/50 splitter SL for example of the type disclosed in FIG. 4 splits incoming beam in parallel beams of equal power. The splitter SL has a polarization preserving coating. One of the split beams is directed via retarder plate λ/2 to rotate the polarization of one the split beams over 45° in order to create a phase difference between two orthogonally polarization components. The polarization splitter SP1, SP2, further splitter SL and retarder λ/2 are formed by respective optic coatings provided on an interface of a respective optic element, in such a way that the interfaces are positioned in the telecentric beam of the second telecentric imaging lens group L3. Due to the telecentricity, the optic behavior is virtually independent of the location in the field image. In the present embodiment, in both branches after the splitter SL, polarizing beam splitters SP1 and SP2 direct s- and p components of the incoming beams to exit ports, in order to produce four polarization phase stepped images at different phases.

The aerosol detection system can be created for all wavelength ranges of interest, provided that the polarization effects in the optical components can be kept within an acceptable range, with a telescope of a refractive type to preserve the polarization states.

Side by side in one exit port there are two images, with a 90° phase step between them. In total, four images are obtained on two detectors with polarization phase steps δ equal to 0°, −45°, +45° and 90°, for a four bucket phase retrieval algorithm. From these four images the overall intensity can be obtained, as well as the modulation depth (degree of polarization) and the phase (angle of polarization).

In FIG. 2 alternatively the splitter SL may be combined with the wavelength filter λ in/near the first telecentric field image F. Accordingly, the field image can be powersplit in a 50/50 beam, where one of the split beams is directed via a retarder plate λ/2 to rotate the polarization of one of the split beams over 45° in order to create a phase difference between two orthogonally polarization components. In both branches, polarizing beam splitters SP1 and SP2 direct s- and p components of the incoming beams to exit ports. In this embodiment, converging lens group L2, pupil stop A4 and second telecentric imaging lens group L3 are provided for each detector d, in order to produce four phase stepped images at different phases; and said polarization splitter, further splitter and retarder are positioned in the telecentric beam of the first telecentric imaging lens group L1; instead of second lensgroup L3. Due to the amount of extra optics (glass) this embodiment is less advantageous than the previous one but still offers the advantage to have less optical components before the polarization splitter elements, thus reduces the risk of polarization influencing by the system.

In FIG. 3, in a further embodiment, instead of power splitting separate parallel branches may alternatively be formed of polarization splitters, with one branch having 45° rotation relative to the other by retarder λ/2. Since the images are simultaneously provided with angle and polarization preserving optics, they can be combined in a controller coupled to the detector detectors at the image plane, arranged to provide difference images as a function of corresponding pixel values of the image sensors to produce an image at a spatially resolved polarization state corresponding to said aerosol substance.

Figure 4:
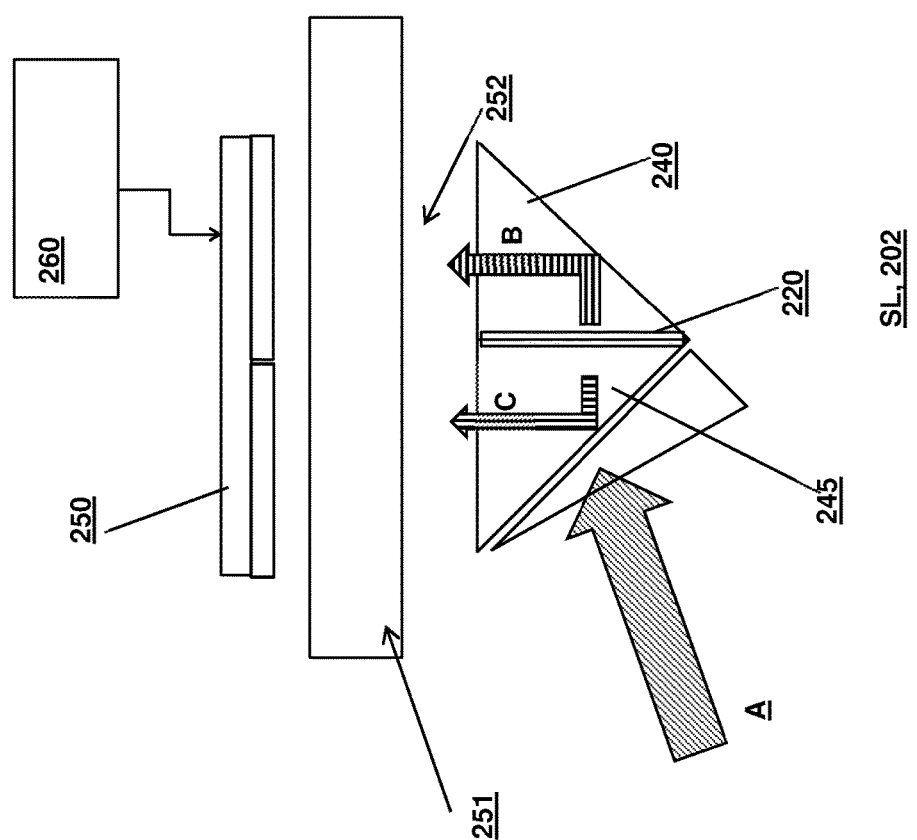
FIG. 4 shows a splitter as part of the embodiments of FIG. 1-3.

In FIG. 4 a power splitter SL, 202, detector 250 and controller 260 are depicted in some detail. The splitter section 202 may be combined with relay optics 252 including a second telecentric imaging lens group 251 arranged to generate a telecentric beam at a detector 250. Semi transparent splitter layer 220 transmits with polarization preservation incoming beam into branches 240, 245. A remaining part is reflected from the semitransparent layer 220 into another branch, thereby functioning as a splitter to produce first and second branches via relay prisms 240, 245.

Figure 5:
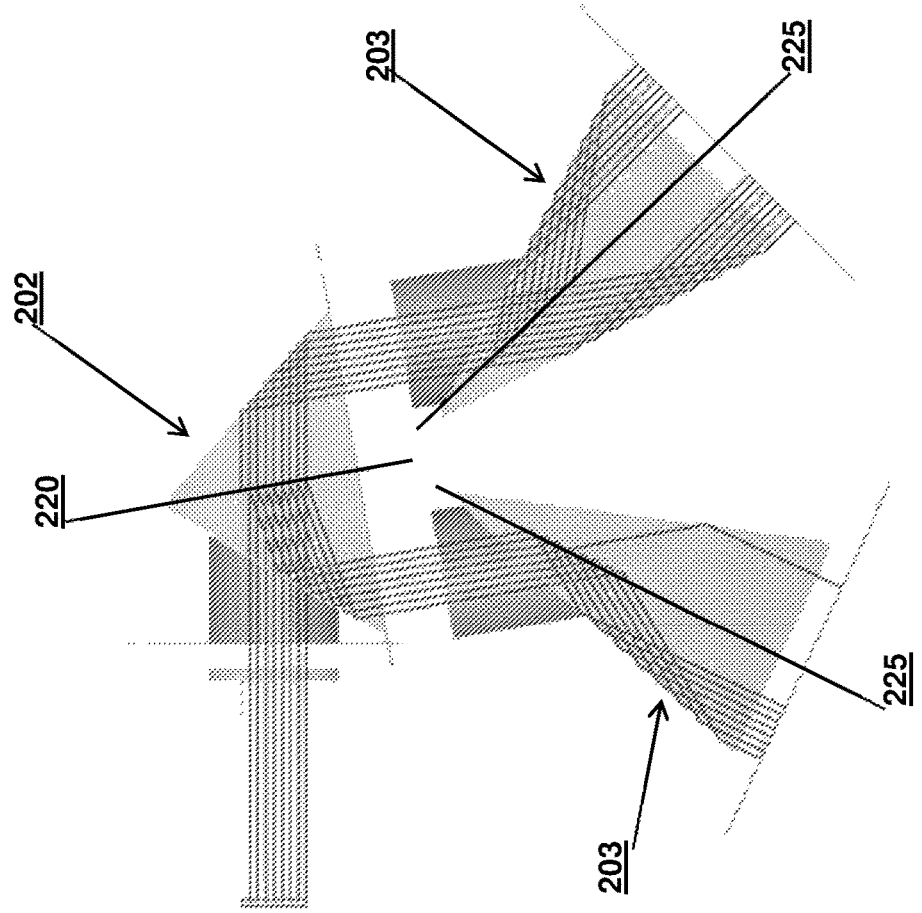
FIG. 5 provides an arrangement of power splitter and polarization splitter to arrive at four simultaneously measured polarization stepped images.

In FIG. 5, in more practical detail of a suitable splitter optics is shown displaying splitter block 202 with a power splitting semi transparent interface 220 and polarization splitter 203 with interfaces 225. Importantly, the ray paths preferably impinge and/or traverse the interface layers 220 and 225 in normal (i.e. perpendicular) fashion by telecentric ray paths, so that the system is substantially insensitive polarization influencing.

Figure 6:
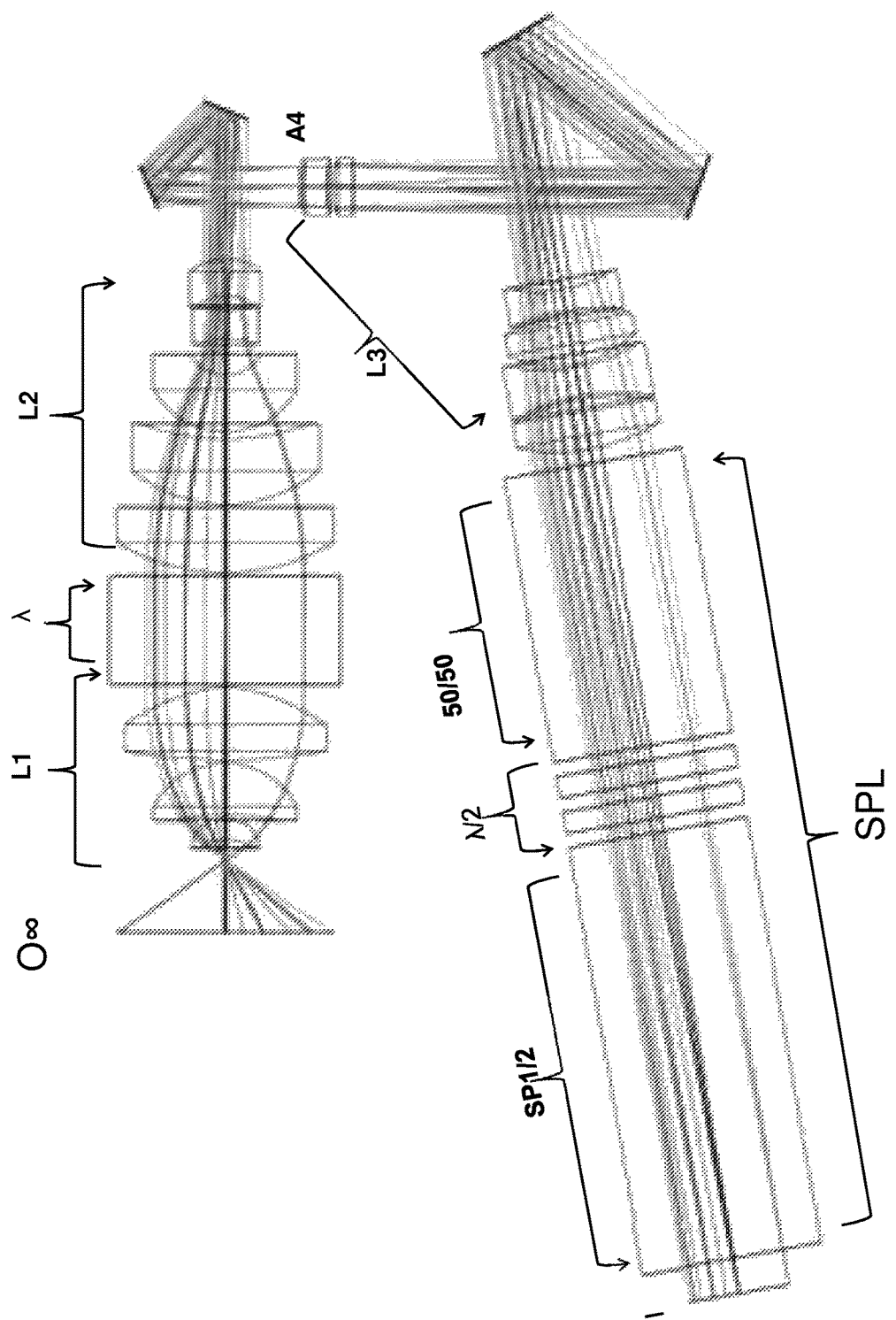
FIG. 6 shows a practical structural view on the embodiment of FIG. 1

In FIG. 6 a realistic design of the aerosol detector is shown with ray paths of the object plane at infinity (earth surface) to the detector at the image plane I. A corresponding structure is shown in FIG. 6. First telecentric lens group L1 comprised of three fused silica lenses is placed in front of the telecentric field image at λ. Second lens group L2 (five sublenses) direct the light via relay mirrors to pupil stop A4. Third lens group L3 (six sublenses), including two folding mirrors direct the light towards a power splitter, retarder (one of the split beams) and polarizing splitters (both split beams). Said splitter optics SPL, in particular said polarization splitter SP1/2, further splitter SL 50/50 and retarder λ/2 are positioned in the telecentric beam of the second telecentric imaging lens group L3.

Figure 7:
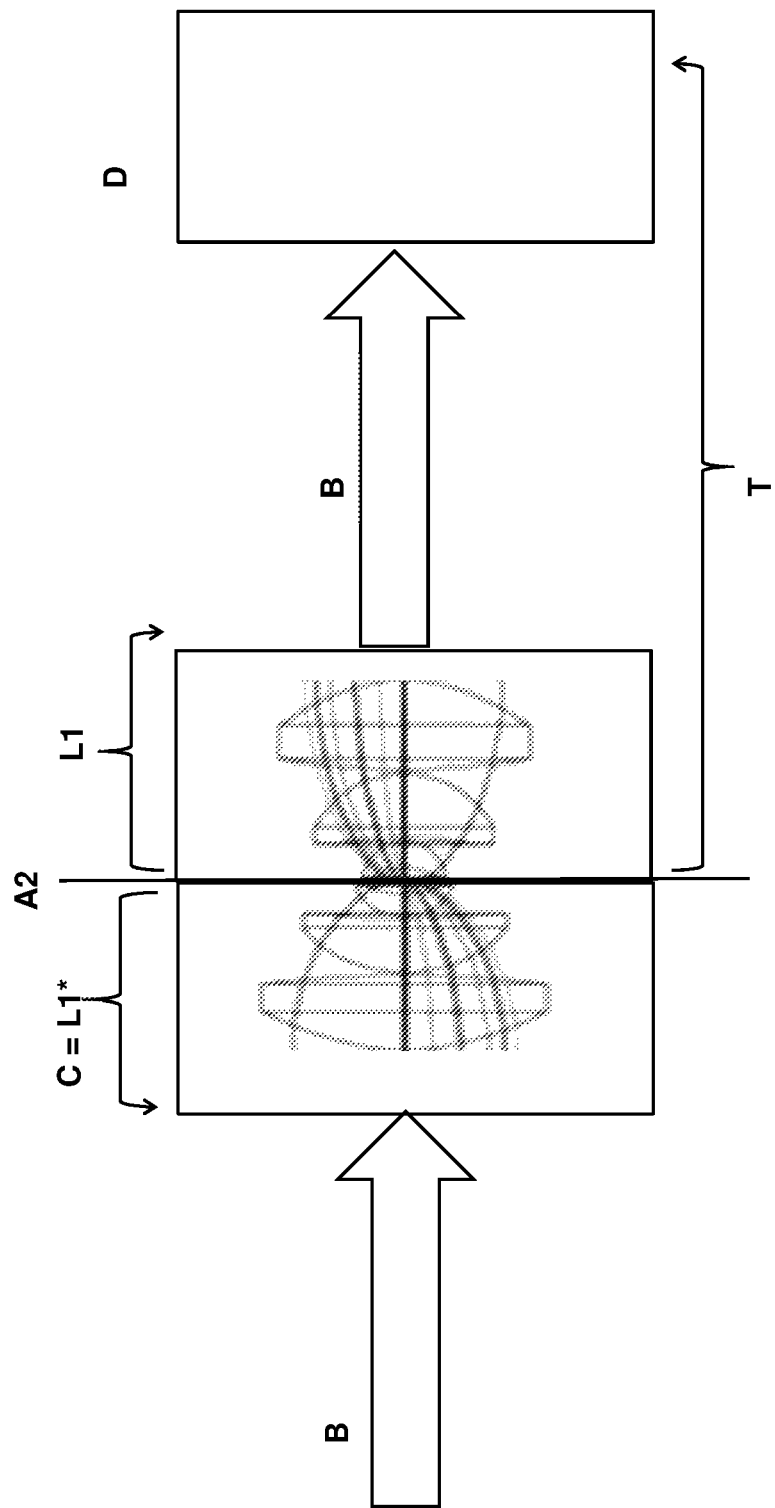
FIG. 7 shows a calibration unit for an aerosol detector system according an embodiment.

FIG. 7 shows an important enhancement of the wide field polarization preserving telescope T as shown in previous embodiments. Telescope T has telecentric imaging optics L1 for imaging the earth surface onto a detector. Advantageously, a calibration unit C is dimensioned as inverse to the first telecentric lens group, i.e. is provided with a mirrored lens group L1*, that has an imaging symmetry respective to entrance pupil. In this way a calibration beam B corresponding to about 100×100 m is imaged by telescope T onto detector D with excellent homogenous quality, so that the detector can be calibrated easily. This calibration unit functions by virtue of a short imaging distance between entrance pupil and first field image. A typical imaging distance lies between 0.1 cm and 5 cm, so that the calibration unit can be provided compact and movable before the image aperture. The unit need not be exactly mirror symmetrical, as long as the field image can be telecentrically imaged on an entrance pupil of the calibration unit C.

Figure 8:
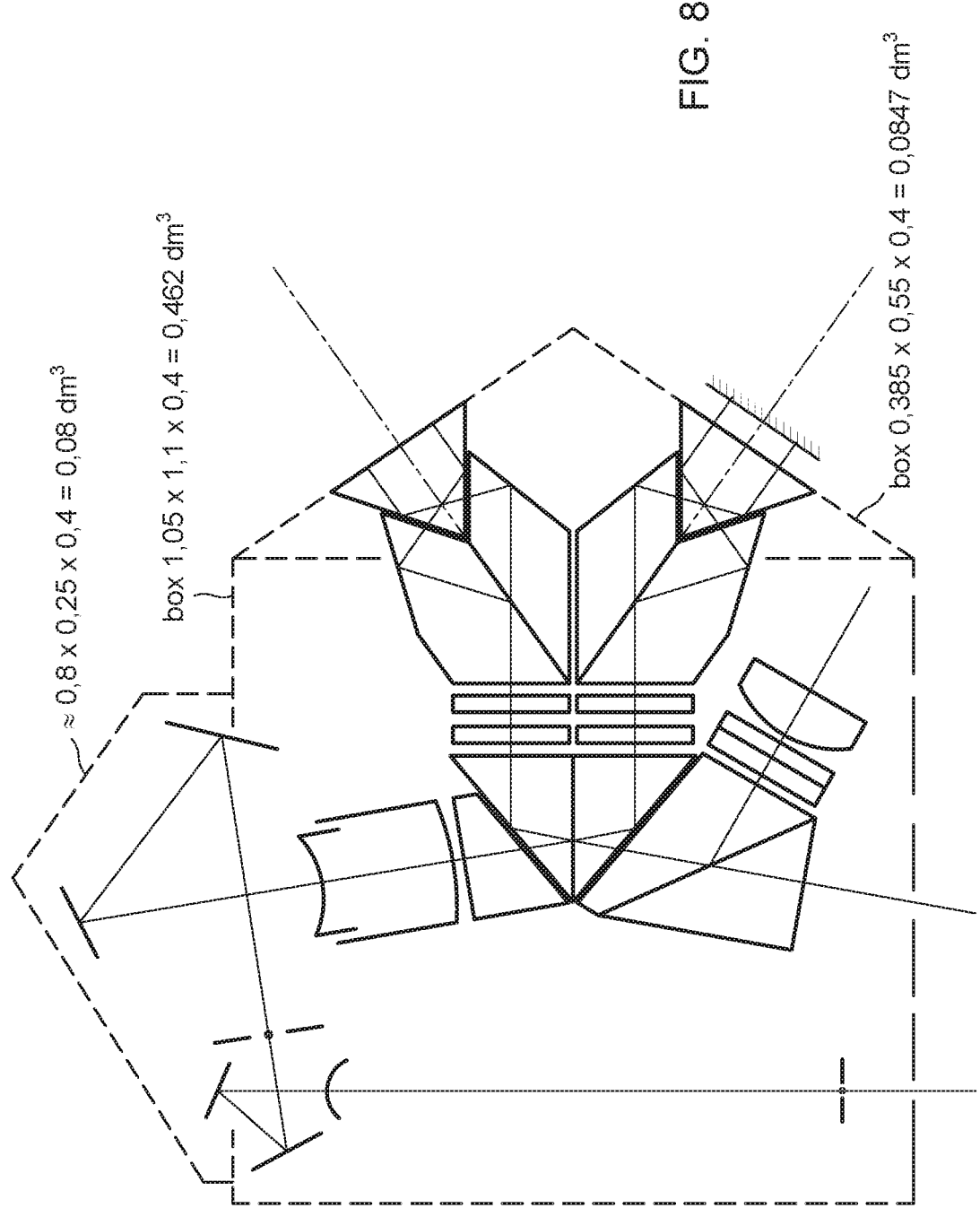
FIG. 8 shows a realistic schema showing the setup for construction within a box.

FIG. 8 shows a realistic schematic wherein it is shown that the embodiments can be carried out in a compact design e.g. a box of about 1×1×0.5 dm$^3$ The disclosed embodiments are only depicted by functional elements, i.e. most of the powered optics used for imaging has been left out. Practical embodiments may therefor be enhanced by functional features represented by optical elements having the same functional effects.

The invention claimed is:

1. An aerosol detector system for spatially and angularly resolved detection of an aerosol distribution in an area, the detector system comprising:
  a controller;
  a detector; and
  a wide field polarization preserving telescope (telescope) having telecentric imaging optics for imaging the area onto the detector;
  wherein the detector receives multiple polarization phase stepped images imaged by the telescope, wherein the controller is coupled to the detector and arranged to provide a difference image as a function of corresponding pixel values of said multiple polarization phase stepped images to produce an image ata spatially resolved polarization state corresponding to an aerosol substance, wherein the telescope comprises a first telecentric imaging lens group and a wavelength filter positioned in a field image of a first telecentric beam generated by the the first telecentric imaging lens group to define a spectral range of interest, wherein the telescope further comprises:
  a converging lens group converging the first telecentric beam to a pupil stop;
  relay optics including a second telecentric imaging lens group arranged to generate a second telecentric beam; and
  splitter optics, comprising a power splitter, a polarization splitter, and a half-wave retarder to create multiple branches with phase stepped images at different polarizations, and wherein the detector comprises multiple image sensors positioned in imaging planes in said branches;

wherein the splitter optics, the splitter, the polarization splitter and the half-wave retarder are positioned in one of a group consisting of:

the second telecentric beam of the second telecentric imaging lens group, and the first telecentric beam of the first telecentric imaging lens group having, for each of the multiple branches, a further telecentric imaging lens group inserted.

2. The aerosol detector according to claim 1, wherein of the splitter optics, the splitter, the polarization splitter and the half-wave retarder are positioned in the second telecentric beam.

3. The aerosol detector according to claim 1, wherein of the splitter optics, the power splitter, the polarization splitter and the half-wave retarder are positioned in the first telecentric beam and wherein for each of the multiple branches a further telecentric imaging lens group is inserted.

4. The aerosol detector according to claim 1, further comprising a calibration unit that images the field image of the first telecentric beam on an entrance pupil of the calibration unit, for providing a homogenous telecentric calibration beam.

5. The aerosol detector according to claim 4, wherein the calibration unit is dimensioned as inverse to the first telecentric lens group.

* * * * *